United States Patent [19]
Hossain et al.

[11] Patent Number: 5,754,620
[45] Date of Patent: May 19, 1998

[54] APPARATUS AND METHOD FOR CHARACTERIZING PARTICLES EMBEDDED WITHIN A THIN FILM CONFIGURED UPON A SEMICONDUCTOR WAFER

[75] Inventors: Tim Z. Hossain; Donald A. Tiffin, both of Austin, Tex.

[73] Assignee: Advanced Micro Devices, Inc., Sunnyvale, Calif.

[21] Appl. No.: 713,497

[22] Filed: Sep. 13, 1996

[51] Int. Cl.$^6$ .................................................. G01N 23/223
[52] U.S. Cl. ............................. 378/45; 378/44; 378/84
[58] Field of Search ................................. 378/44, 45, 50, 378/86, 84

[56] References Cited

U.S. PATENT DOCUMENTS

| | | | |
|---|---|---|---|
| 5,029,337 | 7/1991 | MacKenzie et al. | 378/44 |
| 5,220,591 | 6/1993 | Ohsugi et al. | 378/45 |
| 5,274,688 | 12/1993 | Grodzins | 378/50 |

OTHER PUBLICATIONS

Siemens Energy & Automation, Inc. Analytical Instrumentation, "Direct–Drive Rotating Anode X–ray Generator," Printed from Internet on Aug. 21, 1996, 4 pages; FR591 Rotating Anode Generator, Printed from Internet on Aug. 21, 1996; 1 page.

"X–Ray Tube Anatomy—Anode Target," X–Ray Tube Anatomy—Anode Shaft, X–Ray Tube Anatomy—Anode Rotor, X–Ray Tube Anatomy—Anode Portion of the Tube, X–Ray Tube Anatomy—Filament Circuitry, Printed from Internet on Aug. 21, 1996, 5 pages.

TXRF (Total Reflection X–Ray Fluoresence), Printed from Internet on Jul. 19, 1996, 2 pages; "Totalreflexions–Röntgenfluoreszenzanalyse."2 pages; Simultix 10/11, 3 pages; Simultix 10S, Simultix 11S, 2 pages, X–Ray Analytical Equipment—UltraX 18, 2 pages; Printed from Internet on Jul. 19, 1996.

"Improvement of Manufacturing Techniques Using Silicon Wafers," Nov. 10, 1995, 1 page; Charles Evans & Associates—Specialists in Materials Characterization—Summary Table of Surface Analytical Techniques, 3 pages; XRF Analytical Methods at Northwest Research, 3 pages; ALS News vol. 11, Jan. 31, 1995, 3 pages.

LaVoie, M.A., et al., "Total reflection x–ray fluorescence analysis of plarized semiconductor product wafers," J. Vac. Sci. Technol. A 14(3), May/Jun. 1996, 3 pages.

Diebold, Alain C., "Calibration issues for total reflection x–ray fluorescence analysis of surface metallic contamination on silicon," J. Vac. Sci. Technol. A 14(3), May/Jun. 1996, 5 pages.

Strobel, Howard A. et al., *Chemical Instrumentation: A Systematic Approach,* 1989 by John Wiley & Sons, Inc., pp. 723–777.

Stroebel, Howard A. et al., *Chemical Instrumentation: A Systematic Approach,* 1989 by John Wiley & Sons, Inc., pp. 780–817.

Michette, Alan G., *Optical Systems For Soft X Rays,* 1986 by Plenum Press, pp. 1–35.

IBM Corporation, "Total Reflection X–Ray Fluorescence Spectrometry (TXRF)," Printed from Internet on Aug. 13, 1996, 2 pages; Charles Evans & Associates—Specialists in materials Characterization—Detection Limit vs. lateral Resolution, Printed from Internet on Aug. 13, 1996, 1 page. Taylor, Larry R. et al., *Instrumental Methods for Determining Elements,* 1994 by VCH Publishers, Inc., pp. 211–261.

*Primary Examiner*—Don Wong
*Attorney, Agent, or Firm*—Kevin L. Daffer; Conley, Rose & Tayon

[57] ABSTRACT

An apparatus and method are presented for determining the identity and quantity of elements embedded within a thin film. A radioisotopic source produces a beam of primary x-rays which impinge at near-grazing angles upon a sample consisting of a thin film and an underlying semiconductor substrate. The beam of primary x-rays cause the emission of characteristic secondary x-ray photons from the thin film of the sample. These secondary x-ray photons are detected by a detector positioned above the sample. The detected X-ray photons are counted and their energies are determined, allowing for the determination of the identity and quantity of elements within the thin film.

29 Claims, 4 Drawing Sheets

APPARATUS AND METHOD FOR CHARACTERIZING PARTICLES EMBEDDED WITHIN A THIN FILM CONFIGURED UPON A SEMICONDUCTOR WAFER

BACKGROUND OF THE INVENTION

1. Field of the Invention

This invention relates to semiconductor wafer fabrication, and more specifically to a non-intrusive apparatus and method for determining the composition and quantity of a specific ("targeted") atomic species embedded within a thin film proximate to the surface of a semiconductor topography using X-ray fluorescence spectroscopy employing a radioisotopic source.

2. Description of the Relevant Art

As device dimensions continue to shrink in the microelectronics industry, the ability to accurately characterize semiconductor processes and the materials associated with such processes becomes more critical. Characterizing thin films is especially important, for the effectiveness and reliability of thin films play an important, central role in semiconductor technology.

In order for a thin film to be effective, it must conform to strict electrical, chemical, and structural requirements. Because the tolerances are becoming smaller as microelectronic device sizes decrease, it is crucial to devise a method and corresponding apparatus to measure certain important characteristics of thin films so that they may function properly. Motivations for thin film analysis exemplify the need for accurate characterization of thin films and specifically the atomic characteristics of elements within those films. At present, no single, conventional analytical technique can characterize in a simple, accurate and cost-effective manner many atomic species found within a thin film.

The importance of atomic characterization (i.e., quantity and type of chemical elements) is needed to ensure proper thin film performance. The importance of atomic characterization is described henceforth as a mechanism for determining the effectiveness in curtailing certain problems: electromigration (voiding), internal stress (tensile and compressive), hillock formation, clumping, migration, etc.

Electromigration refers to the movement of atoms in the presence of a current density. A metal ion subjected to a high current density flowing across a metal experiences opposing forces. One force is brought about by a current-generating electric field while the other force is due to collisions with current-carrying electrons within the metal. The force due to collisions dominates; consequently, the metal ions drift in the same direction as the flowing electrons. The mass transfer represented by the flowing metal ions can lead to the formation of voids in the metal. Due to small, sometimes imperceptible, variations in the surface of the metal, the drift velocity of metal ions may vary as a function of position. This may result in a "pile-up" of metal in some regions and a corresponding "void" in other regions. Voiding caused by electromigration in metal films can create catastrophic errors in circuit functionality, especially in circuits where current densities may routinely exceed $10^6$ amperes/cm$^2$. Current densities of this magnitude greatly enhance mass transfer of metal ions and lead to relatively rapid void formation.

Several different approaches have been explored to reduce electromigration voiding. One such approach involves purposefully introducing impurities into thin metal films (e.g., introducing silicon atoms into thin aluminum films). The introduction of impurities affects metal grain size, which, in turn, affects diffusion and mass transport rates within the metal. A decrease in the metal transport rate decreases the occurrence of voids caused by electromigration. As the metal transport rate decreases, fewer metal ions pile up. With fewer pile-ups, fewer voids form within the metal. Silicon, titanium, and copper have all been introduced into thin metal films to combat voiding due to electromigration.

Introducing impurity atomic species (i.e., atoms such as silicon or copper not normally associated with a receiving film) into a thin film such as a thin metal film comprising aluminum can lead to problems if too many or too few of the foreign atoms are introduced. An optimal amount of introduced atoms will, however, reduce problems associated with electromigration voiding. For instance, introducing too much silicon into an aluminum line can lead to such a significant decrease in conductivity rendering the aluminum useless as a conductor. Also, changing the elemental composition of a metal line changes the structural and thermodynamic behavior of the material. These changes, especially as thin film tolerances become smaller, can cause severe problems as the subsequent processing steps are performed.

It is important when minimizing electromigration voids that the added atomic species be accurately and quickly monitored in situ. One may employ a set of experiments in which the atomic species added to the thin film are targeted for analysis both for identity and quantity. Subsequently, electromigration effects could be studied and correlated with the quantity and identity of those targeted atoms. After varying the amount of foreign substance, one may determine an optimum amount by which the targeted atoms achieve beneficial results. Thus, it would be desirable to be able to monitor, during processing, the amount and identity of targeted atomic elements being added to a thin film of interest. The targeted atomic elements are henceforth defined as those having a concentration typically less than the elemental species which forms the film in its original state (prior to the addition of the targeted species). For example, if the film comprises essential polysilicon (with some other trace elements), then the original-species element is essentially silicon. If the film is metal, then the essential species is aluminum or aluminum alloy. The targeted atomic species is therefore an element added to the essential species to aid in its performance but is not necessarily a base or "essential" element. For example, silicon can be added as a targeted atomic element to a metal film comprising essentially titanium to enhance the electromigration performance of the metal film.

Voids and cracks may occur in metal films from mechanical stress. Tensile stress in metal films during heating can exist because of a mismatch in the coefficients of thermal expansion of a metal line and its underlying silicon substrate. In response to the stress, it is believed that metal atoms diffuse into grain boundaries from neighboring grains, resulting in the formation of metal voids. Once again, grain size plays an important role in this voiding process because of its influence on mass transport and diffusion. To combat the problems associated with voiding due to stress, impurity species can be added. The impurity species represent concentrations less than the essential elements originally contained within the metal i.e., aluminum or titanium. The impurity species being added help adjust the grain size in such a way as to relieve the stresses which may lead to voids and cracks.

Again, it is important to achieve a proper balance by introducing an optimal amount of foreign atoms but no more or no less than that amount. If too many or too few targeted atoms are added, then entirely new problems may occur. A device and method for measuring the amount and identity of added atoms embedded within a thin film is thus crucial for a reliable solution to the problem of stress-related cracks and voiding. One may envision an inexpensive, accurate monitoring station which could be placed within a fabrication facility at several locations for determining whether processing parameters are introducing an optimal amount of foreign atomic species into the film of interest, given the specific application of that film. If the monitoring station signaled that too little or too much foreign substance was being introduced, engineers could stop the process, quickly determine the problem, and correct it. Again it would be desirable for the monitoring station to only measure the properties of the targeted thin film rather than the properties of the underlying layers or substrate. Confining measurements to the thin film of interest would ensure that only atoms within that film are being counted.

Another processing problem encountered with thin metal films is hillock formation. Hillocks are protrusions in the surface of a thin film metal layer which may cause problems catastrophic to the operation of a circuit. For instance, a hillock may become prominent enough to extend through an overlying dielectric to a conductive layer placed on that dielectric. Hillocks are believed to be formed because of a large disparity between the thermal coefficients of expansion for thin metal films and for silicon substrates. Upon heating, thin metals expand more than the underlying silicon substrate. However, because the thin film is firmly adhered (either directly or indirectly) to the surface of the substrate, it is physically constrained from fully expanding. The inability to completely expand builds up compressive stresses in the film which are subsequently relieved, in part, by the formation of hillocks on the surface.

Hillocks may also come about, in part, because of the high rate of vacancy diffusion in a thin metal film. Relief of the compressive stresses mentioned above may occur through the process of vacancy migration away from the hillock site. This vacancy migration contributes to the growth of hillock structures. Stress relief via vacancy migration is dependent upon the diffusion rate in the thin film metal. The diffusion rate may be influenced by the purposeful addition of impurities into the thin film. The addition of such impurities can effectively "plug" the grain boundaries of the metal, reducing the effective diffusion rate and inhibiting vacancy migration and hillock growth.

In each of the above examples, a viable solution to each problem included the introduction of minor amounts (relative to the original essential amounts within the film) of impurity atoms into the film of interest. The amount of impurity thus introduced is extremely important so that reproducible, beneficial results may be obtained. It would thus be desirable to devise a method and apparatus which could accurately, quickly, and inexpensively evaluate the quantity and composition of atomic species purposefully added to the thin film. Such a devise and method could become a part of the processing procedure, serving as a check of processing integrity. Because it could function as a relatively inexpensive monitoring station, many could be set up within a fabrication facility.

Besides the introduction of material directly into thin films, it has been found that the use of a thin film diffusion barrier layer can be helpful in indirectly introducing impurities into adjacent thin films. For example, the use of a diffusion barrier may decrease many of the problems associated with adding silicon directly to aluminum films as the metal film is deposited.

When silicon is added directly to a thin aluminum film, the silicon may nucleate and form "clumps" within the film. Clumping occurs because the solid solubility of silicon in aluminum decreases with decreasing temperature. Therefore, during the cooling cycle of a thermal anneal, aluminum becomes saturated with silicon until the silicon begins to precipitate. Silicon precipitates can cause significant problems. For example, in smaller contacts, silicon precipitates may significantly increase the resistivity of the contact. In thin aluminum lines, silicon precipitates effectively narrow the cross-section of the metal line, increasing the current flux across the metal. Such an increase in the current flux increases undesirable electromigration effects such as voiding.

To circumvent the difficulties associated with the direct addition of silicon into aluminum, it is possible to make use of a barrier thin film sandwiched between the silicon substrate and the thin film metal. Such a thin-film barrier may help curtail migration of atomic materials between the silicon substrate and the metal layer. For instance, 250 angstroms of titanium, doped with a predetermined amount of silicon may be introduced between a silicon substrate and an aluminum thin film. Such a barrier, termed a sacrificial barrier, would allow for limited diffusion of silicon into the aluminum thin film. The controlled diffusion of silicon into the aluminum not only reduces formation of voids due to electromigration but also reduces the formation of hillocks by affecting the grain size of the aluminum and thus the diffusion rates of the metal.

Polysilicon may also serve as a barrier between a substrate and a thin aluminum film. Under high current stresses, silicon from the polysilicon may be transported into the silicon. This mass transport, if in proper proportions, may then reduce the occurrence of voids and stresses in the aluminum film.

In order for a barrier layer to effectively control diffusion of materials into a thin film, it is essential that a proper quantity and type of impurity be present within the barrier thin film. If, for example, a barrier layer is deposited with too many impurity atoms present, subsequent diffusion into a metal layer can lead to decreased conductivity or to other problems such as the formation of precipitates, voids, additional stress, or additional strain.

Currently, no one analytical tool possesses all the characteristics needed for the effective monitoring of beneficial atomic impurities (i.e., "targeted" atomic species) within a thin film. In other words, no current technique allows for accurate, reliable, inexpensive, portable, non-destructive characterization of materials embedded within a specified thin film irregardless of the underlying film composition. Although no current analytical method solves the problems discussed above, it is nonetheless useful to discuss some of the current analytical tools used today in the semiconductor industry, for these tools do point out some difficulties and shortcomings associated with characterizing thin films.

The microelectronics industry currently uses several different analytical tools for characterizing materials present in semiconductor processes. One of the more prevalent analytical methods in industry today is Secondary Ion Mass Spectroscopy (SIMS). In SIMS, a sample to be studied is bombarded with a primary beam of energetic ions. These ions sputter away ionized particles, secondary ions, from the surface of the sample. Secondary ions are directed into a mass spectrometer which identifies the ions as a function of their mass to charge ratio. Continued sputtering dislodges particles and secondary ions located below the surface of the sample. Thus, SIMS has the ability to analyze elements embedded within the sample as a function of sample depth. For example, one may ascertain from SIMS data that $10^{19}$ atoms of boron per $cm^2$ reside at the surface of a silicon sample while $10^{17}$ atoms of boron per $cm^2$ reside one micron below the surface. Thus, in principle, SIMS could, and is, used to measure the amount of material embedded within a thin film. However, SIMS does not meet the requirements of being an inexpensive, non-destructive technique requiring little maintenance, having the ability to serve as a portable monitoring station.

Although SIMS depth resolution, lateral resolution, and sensitivity continue to improve year after year, several drawbacks are inherent with SIMS measurements. The biggest drawback is the fact that SIMS is a destructive technique. SIMS sputters away layer after layer of material from the surface of the sample; thus, it is not feasible to use SIMS as a bench-top process control station which could monitor the amount of material embedded within a thin film. Also, SIMS is a very bulky, complex, expensive method requiring complicated, maintenance-intensive machinery. For instance, SIMS instruments typically occupy an entire room in a midsized laboratory and consist of several vacuum pumps, valves, powerful magnets, energy filters, ion sources, and complex data analysis tools.

Another technique commonly used in the semiconductor industry is Auger emission spectroscopy (AES). In AES, an energetic, primary electron beam is directed at the surface of a sample. The primary electron beam interacts with atoms at and near the surface of the sample, dislodging electrons from energy shells of the sample. As an energy shell is vacated, an electron within a higher energy state may fill the vacant position. The electron filling the once-vacant state releases energy characteristic of the transition in energy levels. This energy then interacts with the atom and ejects an electron of a lower energy state. Such an ejected electron is termed an Auger electron and has energy characteristic of the process which caused its ejection. Because an ejected Auger electron has an energy characteristic of the energy levels of the atom from which it is ejected, one may determine the composition of the sample being studied by measuring the Auger electrons. Because Auger electrons cannot escape from great depths within the bulk of a sample, AES is a surface-sensitive analysis technique. It is commonly used to study materials present at a depth within fifty Angstroms from the sample's surface.

In order to study the composition of a sample deeper below the surface, it is necessary to sputter away atoms from the surface of the sample being studied. Thus, to measure the quantity of materials embedded within a thin film deeper than approximately fifty Angstroms, ion sputtering must often be used. AES may be performed in a raster scan mode, allowing for the study of Auger electrons as a function of three-dimensional position. This mode of operation is called Scanning Auger Microprobe (SAM) and is becoming more prevalent in the semiconductor industry. Although providing excellent lateral resolution and possessing the ability to probe very small areas, AES and SAM suffer from the same major drawback as does SIMS—when probing beneath the surface of a thin film, sputtering is required which effectively destroys the sample. Also, like SIMS, AES requires expensive, complex machinery which may become maintenance intensive. A typical AES system consists of vacuum pumps (AES is most effective when carried out at pressures of approximately $10^{-10}$ torr and lower) and an ion beam for sputtering the sample.

Another technique utilized in microelectronics characterization is X-ray Photoelectron Spectroscopy (XPS). In this technique, an X-ray beam is directed at a sample, and the interaction of X-ray photons with the atoms of the sample causes the ejection of electrons from the sample. The kinetic energy of ejected electrons is characteristic of the sample being studied. Like AES, only electrons from the top 1–10 monolayers are emitted from the sample. Thus, XPS is similarly a surface-sensitive technique. Like AES, if XPS is to probe within the thin film, destructive sputtering must be employed. Also, similar to AES, XPS systems are quite complex, expensive, and may become maintenance intensive. A typical system consists of powerful vacuum pumps, an electrostatic energy analyzer, and a complicated data analysis system.

X-ray Emission Spectroscopy (XES) is yet another technique in use in the semiconductor field. In XES, an electron beam, typically the same electron beam used in conjunction with Scanning Electron Microscopy, impinges upon a sample, creating electron vacancies. When these vacancies are filled, characteristic secondary X-ray photons may be emitted. Emitted secondary X-ray photons are characterized using one of two basic detection schemes. In the first scheme, a crystal analyzer takes advantage of the Bragg angle of emitted radiation to characterize the wavelength of the emitted X-ray photon. In the second scheme, the energy of the X-ray photon is determined using, most commonly, a lithium-drifted silicon detector.

In either detection scheme, secondary X-ray photons are correlated with the elemental composition of the sample being studied. Although a very powerful technique, one major drawback to XES is that secondary X-ray photons as deep as five microns below the surface are sometimes emitted and detected by XES systems. XES is not necessarily able to distinguish materials embedded within a thin film from materials embedded within a silicon substrate. XES may not be a reliable method to measure, for example, the amount of silicon embedded within a thin film of titanium directly above a silicon substrate. In such a case, XES would detect silicon from within the thin titanium film as well as from the silicon substrate.

The final analytical method to be discussed is X-ray Fluorescence (XRF). In XRF techniques, a beam of primary X-rays is directed at the surface of a sample, and the energy levels (or corresponding wavelengths) of resultant secondary X-rays emitted by atoms of elements on and under the surface of the sample are measured. The elemental compositions of materials on and under the surface of the wafer may then be determined from the measured energy levels (or wavelengths) of emitted secondary X-rays.

There are two main categories of XRF: (i) wavelength-dispersive XRF (WDXRF), and (ii) energy-dispersive XRF (EDXRF). In WDXRF techniques, a sample is irradiated with polychromatic primary X-rays (i.e., primary X-rays with many different wavelengths), resultant secondary X-rays are dispersed by diffraction into discrete wavelengths, and intensities of the secondary X-ray photons are measured versus wavelength. Elemental coverage using WDXRF techniques typically can be extended down to boron when analysis is carried out in a vacuum. EDXRF techniques involve irradiating a sample with polychromatic primary X-rays and measuring fluorescent secondary X-ray intensity versus detected secondary X-ray photon energy level. Elemental coverage with commercially-available equipment employing EDXRF techniques typically extends down to sodium.

One drawback to XRF is the presence of background radiation which limits the sensitivity of the device. Primary X-ray photons may loose energy when scattered by atoms of the target material. Such scattered primary X-ray photons which reach the X-ray detector of an XRF instrument create an unwanted background intensity level which secondary X-ray photons must exceed in order to be discerned. Thus the smallest amount of an element which may be detected in a sample using an XRF instrument is largely determined by the background intensity level at the energy level (or corresponding wavelength) associated with characteristic secondary X-rays emitted by that element. The sensitivity of an XRF instrument is thus largely dependent upon the background intensity level, and the sensitivity of an XRF instrument may be improved by reducing the amount of scattered primary X-rays reaching the detector.

To reduce background radiation and to improve sensitivity, the current trend in XRF is a employ more powerful, collimated, polarized sources of primary X-rays. Such sources, by improving sensitivity, are able to detect trace concentrations of elements down to approximately $10^{11}$ atoms/cm$^2$. To understand such a trend, it is first necessary to discuss the current state of X-ray detectors used in XRF, including both conventional X-ray tubes and rotating anode sources.

Figure 1A:
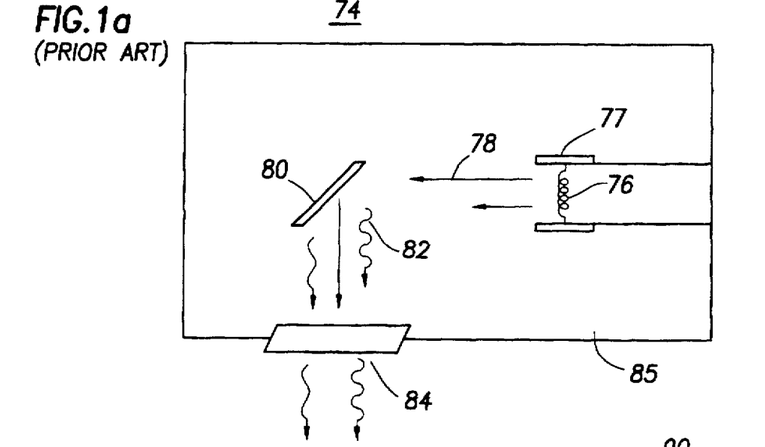
FIG. 1a is schematic diagram of a conventional X-ray tube.

FIG. 1a is a basic schematic of a conventional X-ray tube used in XRF equipment. X-ray tube 74 consists of a cathode 77 containing filament 76 separated a distance from an anode target 80. A steady, large potential difference of 10–100 kilovolts is placed between anode 80 and cathode 76, with the anode being positive relative to the cathode. Creating such a large, steady potential difference requires the use of a large power source. Those power sources normally operate by retrieving power from a main supply through a line stabilizer into a high voltage generator. The high voltage generator rectifies the voltage and stabilizes both the output current and voltage using various stabilizing circuits. Quantitative spectroscopy requires highly-stabilized sources. Any variations in the photon output from a source is referred to as drift and may contribute to significant systematic errors in quantitative analysis.

Responsive to the large potential difference, a current flows through filament 76, heating filament 76 and causing the ejection of electrons 78 into evacuated region 85. The high-energy electrons strike anode target 80, emitting both characteristic and continuous Bremsstrahlung X-ray radiation 82. Bremsstrahlung radiation often termed, braking radiation, arises from electrons slowing down within the anode target 80. Anode 80 typically comprises hromium, rhodium, tungsten, silver, gold, or molybdenum. The choice of anode target may be an important one, for the choice of target affects the relative proportions of characteristic to continuous radiation produced by the X-ray source. If a continuous spectrum is needed for a particular experiment, a metallic target of high atomic number should be chosen.

The X-ray radiation produced at the anode passes through a thin window 84, usually made of beryllium, separating the evacuated region 85 from atmospheric pressure. Window 84 often acts as an X-ray filter, not allowing certain characteristic radiation to pass out of tube 74. The choice of window thickness may also become important, for window thickness too affects the relative proportions of characteristic to continuous radiation.

One of the main design problems associated with X-ray tubes is the effective dissemination of heat generated at the anode. Currents incident on the target will sometimes reach 10–50 milliamps, and with a potential difference in the range of 100 kilovolts, the target may be subjected to 2–3 kilowatts of heat which must be dissipated in order to avoid melting the sample. To alleviate the heating of the sample, water cooling has been utilized but does not always prevent surface melting. Another solution involves rotating the target material (the anode). If the anode is rotated, the heat is effectively spread across more surface area, and melting may be avoided.

Figure 1B:
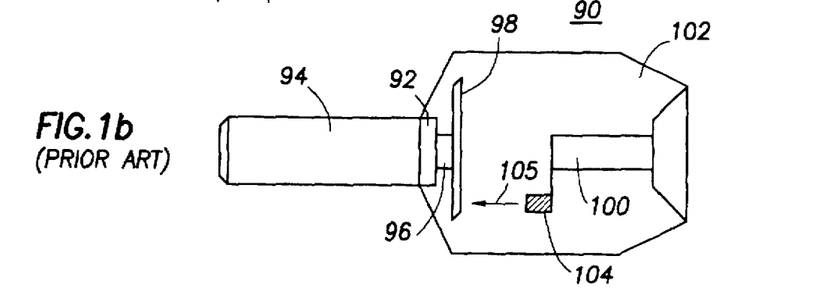
FIG. 1b is schematic diagram of a rotating anode X-ray source.

Powerful X-ray tubes used in many of today's XRF instruments employ a rotating anode source. FIG. 1b shows a typical rotating anode source. Focusing cup 104 contains a filament. Cathode 100 and focusing cup 104 are maintained at a large negative bias relative to rotating anode target 98. Anode shaft 94 rotates anode shaft 96 which in turn rotates target 98. Current runs through the filament housed within cup 104, causing heating and the ejection of energetic electrons 105. The high potential maintained between cup 104 and target 98 causes the acceleration of electrons 105 through evacuated region 102 towards rotating target 98. Upon impact, high power braking radiation is emitted from rotating anode 90. Several materials may be chosen for rotating anode 98, including Cu, Mo, Cr, Co, Ni, Au, Ag, and Fe. The power of today's rotating anode sources may reach upwards of 18 kilowatts.

Such sources, although they provide a powerful source of primary X-rays which improve sensitivity and lower detection limits, are quite expensive and maintenance-intensive. Even conventional X-ray tubes as shown in FIG. 1a require expensive, stabilized high power sources which do not lend themselves to the goal of an inexpensive, compact, portable, reliable, maintenance-free monitoring station for measuring minor concentrations of elements (e.g. elements having a concentration above $10^{15}$ atoms/cm$^2$) embedded within thin films.

Besides their complexity and expense, another drawback of XRF machines is their degree of penetration into a sample being studied. XRF machines employing high-powered X-ray sources may excite atoms well below the surface of the sample being studied. Thus, secondary X-ray photons emitted by the sample may originate a few microns from the surface of the sample. However, as discussed earlier, a method is desired which would confine measurements to thin films and not penetrate to lower levels or to the substrate.

Considering all the prevalent analytical tools in use today in the semiconductor field, no one technique is able to effectively, accurately, inexpensively, and reliably measure the quantity and identity of what is termed "targeted" atomic species of relatively minor concentration elements embedded within a thin film. A device and method which could achieve such characterization of thin films may be used as a multiple-location monitoring station within a fabrication environment to characterize certain processing steps and to ensure that a proper proportion of targeted atomic materials were embedded within thin films. If a proper control mechanism could be applied to thin film technology, many problems such as voiding, cracking, and thin film stress could be addressed and reduced, if not eliminated altogether.

SUMMARY OF THE INVENTION

The problems outlined above are in large part solved by a non-intrusive apparatus and method for determining the composition and quantity of targeted impurity atomic species are embedded within a thin film being measured.

A radioisotopic source is configured to produce a beam of primary X-rays. These X-rays are incident upon a sample having a thin film positioned upon an underlying semiconductor substrate. The angle of incidence (between 0.01 and 5.00 degrees as measured relative to the surface of the sample) and energy of the primary X-rays are such that atoms embedded within the thin film are excited and create electron vacancies. The vacancies are subsequently filled by electrons with higher energy states than the energy states of the vacant positions. These energy-level transitions produce a beam of characteristic secondary X-ray photons emitted from the atoms embedded within the thin film.

The secondary X-ray photons are received by a detector placed directly above the sample. The detector produces an output pulse responsive to the receiving the secondary X-ray photons. This output pulse is proportional to the energy of the detected secondary X-ray photons.

A data analysis unit receives the output pulses and analyzes them to determine the number of secondary X-ray photons received by the detector and their respective energies.

The data analysis unit may present its information as a plot of secondary X-ray photon counts versus secondary X-ray photon energy. Such a plot would consist of peaks representing the elements present within the thin film. Unless the thin film being studied consisted of only one element, at least two peaks would comprise the plot of photon counts versus photon energy. To determine the identity of elements present within the thin film, one would correlate the energy range of each peak with the characteristic energy value for a certain element. Thus, if the plot showed a peak centered about 1.74 keV, one would know that the peak most likely represented silicon atoms embedded within the thin film. To determine the quantity of elements within the thin film, one could employ at least three different methods.

In one method, the ratio of areas underneath each peak in the plot is determined. This ratio would represent the relative ratio of an element within the thin film. Thus, if the area under a silicon peak were 10 (in arbitrary units of area) while the area under a titanium peak was 200 (in the same arbitrary area units), the thin film would contain 5% of silicon relative to titanium.

In another method, the area under a peak is determined along with the quantity of elements in the represented area. That determination is had by using regression data from standard samples having a known composition. Therefore, in the example above, one could measure that the area under the silicon peak was 10. Looking at the appropriate data from standards would then indicate that a silicon peak area of 10, measured under certain conditions (such as count time, primary beam energy, etc.), corresponded to a certain concentration of silicon, given in units of atoms/cm$^2$.

Finally, according to another exemplary method, the area under a peak can be determined and correlated with a standard which shows the relative concentration of the element of interest. Turning again to the example, consider that the area under the silicon peak is 10. One could then look up in an appropriate look-up table data which shows that for a given area under a titanium peak measured under certain conditions, a silicon area of 10 corresponds to a 5% silicon concentration.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

FIGS. 2, 3, 4a, and 4b will be used to describe, in general, the basic processes occurring during X-ray spectroscopy. Quantum mechanics teaches that the energy of an electron within an atom is quantized. More specifically, energy cannot assume any arbitrary value but is instead limited to discrete values within an energy spectrum. This means that an electron in an atom occupies a quantized state with an energy characteristic of that state. The exact nature of the state depends upon many factors such as the potential due to the nucleus and the surrounding electron charge in the atom, which in turn depend upon factors such as the atomic number of the atom itself.

The quantized states of an electron may be described with four basic quantum numbers, n, l, m, and s. The quantum number 'n' is referred to as the principal quantum number (or sometimes the electron level), and in the field of spectroscopy, it represents the 'shell' of the atom in which an electron is most likely to reside. The lowest principal quantum number, n=1, is termed the 'K' shell, n=2 refers to the 'L' shell, n=3 refers to the 'M' shell, and n=4 is the 'N' shell.

Figure 2:
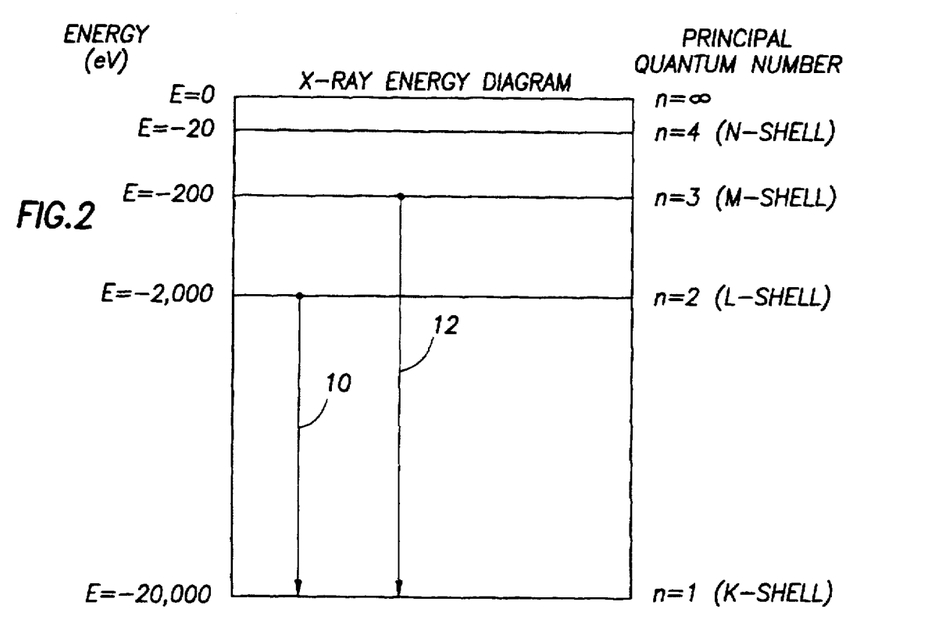
FIG. 2 is an X-ray energy level diagram, showing exemplary electron transitions.

Associated with each set of quantum numbers is an energy characteristic of that set of numbers. In other words, if the state of an electron is known, it has an energy characteristic of that state. FIG. 2, for simplicity, assumes that the energy of the electrons depends only upon the principal quantum number 'n'. Electrons with lower values of n represent electrons more likely to be found closer to the nucleus. Such electrons, as can be seen in FIG. 2, have large, negative energy values. As the principal quantum number increases, the energy becomes larger, until at n=∞ the energy is zero. This energy scheme can be understood alternatively in terms of binding energies. Electrons close to the nucleus (lower n values) are tightly bound to the nucleus. It takes more energy to remove these tightly bound electrons from the atom than it takes to remove a more loosely bound electron. To quantitatively determine the amount of energy it would take to remove an electron from an atom. one must take the difference between the initial and final energy states. Removing an atom from the n=1 state thus requires taking the energy differences between the n=∞ and n=1 states. The n=∞ state is used in the calculation because it represents the energy state of a free electron—an electron not bound to the atom at all. The example of FIG. 2 indicates that n=1 state has an energy of −20,000 eV and the n=∞ state has zero energy. Zero energy simply implies that the atom is free and has no kinetic energy (it is not moving). Therefore, the minimum amount of energy required to free an electron from the n=1 state is:

$$\text{Energy}_{removal} = (0 - (-20{,}000 \ ev)) = 20{,}000 \ eV$$

As can be seen in FIG. 2, the energy spacing between levels becomes smaller as the principal quantum number increases. The spacing between the n=1 and n=2 states is 18,000 eV, while the spacing is only 180 eV between the n=3 and n=4 states. Because of the decreasing spacing of energy levels, it is customary in X-ray spectroscopy to consider levels above n=5 as being, essentially, equivalent (energetically) to the n=∞ state.

Because atoms are quantized, electrons can occupy only discrete quantum states. If FIG. 2 were to represent the full set of quantum states available to an electron, all electrons in the atom would have to reside on the lines labeled n=1, n=2, n=3, or n=4. Again, the line n=□ represents a free electron not bound to the atom, having and energy equal to zero. Quantum mechanics, under the guise of the Pauli Exclusion Principle, teaches that no two electrons may have the same set of quantum numbers. Therefore, if FIG. 2 did represent a full set of quantum numbers, only one electron could occupy a given energy state. Each principal quantum number (n) shown in FIG. 2 has a multiplicity so that n=1 can hold a maximum of 2 electrons, n=2 a maximum of 8 electrons, n=3 a maximum of 18 electrons, etc.

An electron residing in a given state may make transitions to another state within the atom. If an electron in FIG. 2 were to make a transition to another energy level, that level must be vacant. If the level were not vacant, two electrons would reside in a single state, violating the exclusion principle (both electrons would have the same set of quantum numbers—in FIG. 2, the same set would be represented by having the same principal quantum number, n). Due to energy conservation principles, when an electron does make a transition into a vacant state, the energy of the system must not increase or decrease. Reference number 10 indicates an electron residing initially in the n=2 state making a transition to the n=1 state. As can be seen in the energy level diagram, the energy characteristic of the n=2 state is −2000 eV while the energy of the n=1 state is −20,000 eV. Before the transition, the electron can be thought of as representing −2,000 eV of energy. After the transition , the electron will reside in the n=1 state and represent −20,000 eV of energy. The difference in energies before and after the transition is (−2,000 eV−(−20,000 eV)), or 18,000 eV. Because of conservation principles, this excess of energy must be released from the atom.

The necessary release of energy may occur in at least two ways. In the first, the excess 18,000 eV is released in the form of a massless photon. This photon travels, in vacuum, at the speed of light and may be thought of as a wave having a certain wavelength and frequency. The wavelength or frequency of this photon may be calculated using the well known relation:

$$E=h\nu$$

where E is the energy of the photon (equal, in our example, to 18,000 eV), h is Planck's constant, and ν is the frequency of the photon.

In the second method of energy release, the excess 18,000 eV may interact with another electron in the atom, causing its ejection. As a hypothetical example, consider the excess 18,000 eV interacting with an electron in the n=3 state and causing its ejection from the atom. As can be seen in FIG. 2, the ejection process itself would expend 200 eV of energy, so the n=3 electron would be ejected from the atom and have a kinetic energy of 17,800 eV (the energy remaining after being ejected).

Reference number 12 indicates an n=3 electron making a transition to the n=1 state. As explained above, a photon or an electron may be ejected in response to this transition. In the transition represented by numeral 12, the excess energy available to the atom from a n=3 to a n=1 transition is:

$$\text{Energy}_{excess} = (-200 \ eV - (-20{,}000 \ eV)) = 19{,}800 \ eV$$

X-ray spectroscopy labels transitions such as 10 and 12 as K transitions. This means that electrons made a transition from some initial state and ended up in the K shell (the state having principal quantum number n=1).

Mentioned above, in order for an electron transition to take place, there must be a vacancy into which an electron may go. Vacancies may be created in several different ways. A common method is to bombard a sample material with a beam of particles. These particles may be electrons, electromagnetic radiation (photons), or other particles. Upon impact, if the bombarding particles have sufficient energy, they may effectively knock an electron out of its quantized state. More specifically, the bombarding particle may transfer its energy to the electron, causing it to make a transition to a higher energy state, quite possibly causing it to make a transition to the free state, represented by n=∞.

Figure 3:
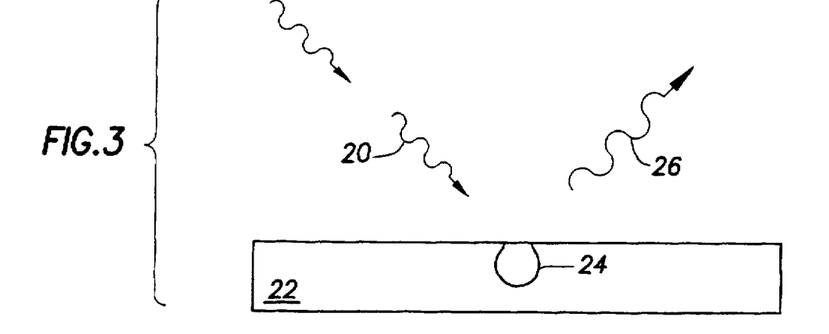
FIG. 3 shows the interaction of a primary beam with a sample, producing a secondary X-ray photon.

FIG. 3 shows a typical process for creating vacancies in a sample 22. Shown is a beam of incoming particles 20. This beam may be made up of particles having mass such as protons or electrons or massless particles such as photons. The incoming beam 20 collides with sample 22 and penetrates into a region 24 of sample 22. The size and shape of region 24 depends upon many factors, not limited to but including the energy of beam 20, the type of particles present in 20, the angle of impact, the composition of sample 22, and thermodynamic conditions. Within the volume of region 24, particles 20 have energy sufficient to cause electron transitions within the atoms making up sample 22 and secondary photons 26 may escape from sample 22.

In the present invention, it is desired that region 24 not extend below the thin film being studied. The present invention of characterizing elements within a thin film requires that elements in underlying layers not be measured, for measuring underlying layers would lead to the overcounting of elements common to both the underlying layers and to the thin film. If the analysis of the quantity of silicon embedded within a thin film is needed, then analysis would certainly not apply to the silicon atoms which reside within the underlying silicon substrate. If region 24 extended within a silicon substrate, however, this overcounting would occur.

Figure 4A:
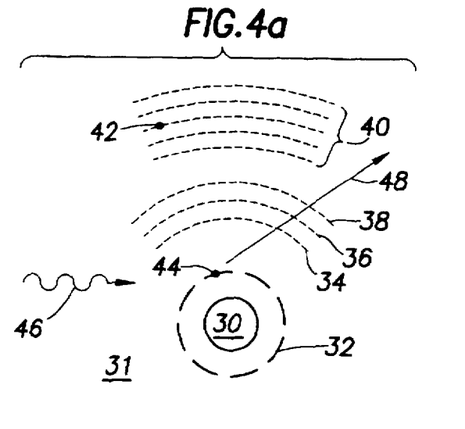
FIG. 4a shows an atom absorbing a primary X-ray photon and correspondingly ejecting an electron from an inner shell.

FIG. 4a depicts a typical excitation process. Electron 44 resides within the K shell 32 of an atom 31 with nucleus 30.

Electron 42 resides in the M shell 40 of the atom. Shown also is the L shell of the atom, depicted by 34, 36, and 38.

In FIG. 4a, radiation 46 is incident upon atom 31. Incident radiation 46 may be either absorbed or scattered by atom 31. In FIG. 4a, incident radiation 46 is absorbed and causes a transition of electron 44. Incident radiation 46 interacts with atom 31 and transfers its energy to electron 44. Because the energy of incident radiation 46 is greater than the binding energy of electron 44, electron 44 is completely ejected from atom 31. This ejection is represented by 48. All energy in excess of the binding energy becomes kinetic energy of ejected electron 44. Thus, in FIG. 4a, incident radiation causes a transition in electron 44 from the n=1 state (K shell 30) to the n=∞ state (the free state).

Figure 4B:
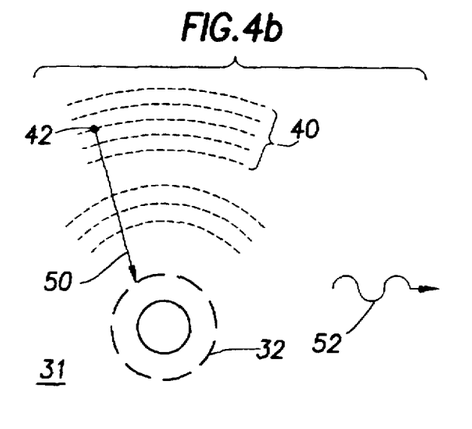
FIG. 4b shows an electron filling a vacancy in an inner shell, releasing a secondary X-ray photon.

FIG. 4b depicts a typical de-excitation process which might follow the excitation process depicted in FIG. 4a. In FIG. 4b, electron 42, initially in M shell 40, makes a transition to fill a vacant state within K shell 32. The transition is depicted by 50. Upon making transition 50, the energy difference between the initial and final electron states of electron 42 is released from atom 31 in the form of a secondary X-ray photon 52. The energy of photon 52 is necessarily less than that of incident radiation 46 in FIG. 4a. Thus, photon 52 is depicted as having a wavelength longer than that of incident radiation 46 in FIG. 4a.

Figure 5:
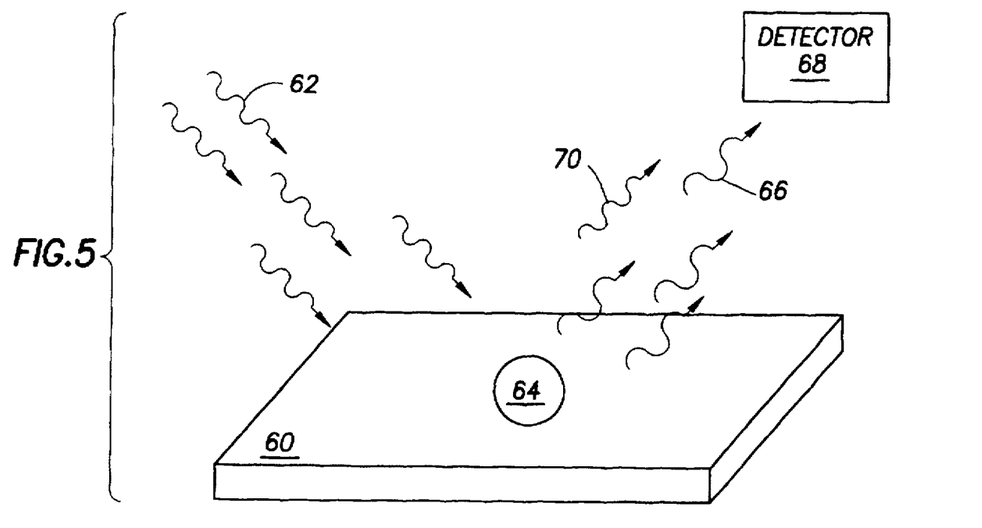
FIG. 5 is a diagram of an exemplary X-ray fluorescence experiment configured according to one embodiment hereof.

As mentioned above, primary X-ray photons may be absorbed or scattered by atoms of a target material. Characteristic secondary X-rays are only emitted when incident primary X-rays are absorbed. FIG. 5 is a perspective view of a target material 60 undergoing analysis in a typical XRF system. An incident beam of X-ray photons 62 is directed at an exposed surface 64 of target material 60. An X-ray detector 68 detects both secondary X-ray photons 66 emitted by target material 60 and primary X-ray photons 70 scattered by atoms of the elements comprising target material 60. Primary X-rays 70 which are scattered by atoms of target material 60 rather than absorbed, loose energy and reach X-ray detector 68, creating an unwanted background intensity level which secondary X-ray photons must exceed in order to be discerned.

In a typical XRF system, depicted in FIG. 5, primary X-rays 62 impact region 64 and penetrate into sample 60. The amount of penetration into a sample is of particular concern for the current invention. In the current invention, it has been stressed that the penetration of primary X-rays must not be such that atoms below a thin film may emit detectable secondary X-ray photons. If atoms below a thin film were to emit detectable secondary X-ray photons, these secondary X-ray photons could not be distinguished from the secondary X-ray photons emitted by atoms of identical composition within the thin film. For example, if one were measuring the concentration of silicon embedded within a thin film of titanium, one could not distinguish X-ray photons emitted by silicon embedded within the thin film from X-ray photons emitted by silicon in the substrate. Thus, if a primary beam of X-ray photons were such as to excite silicon within the substrate, the indistinguishable nature of secondary X-ray photons emitted by silicon atoms would lead to the overcounting of silicon embedded within the thin film (one would be counting the silicon embedded within the thin film in addition to the silicon embedded within the substrate).

Figure 6:
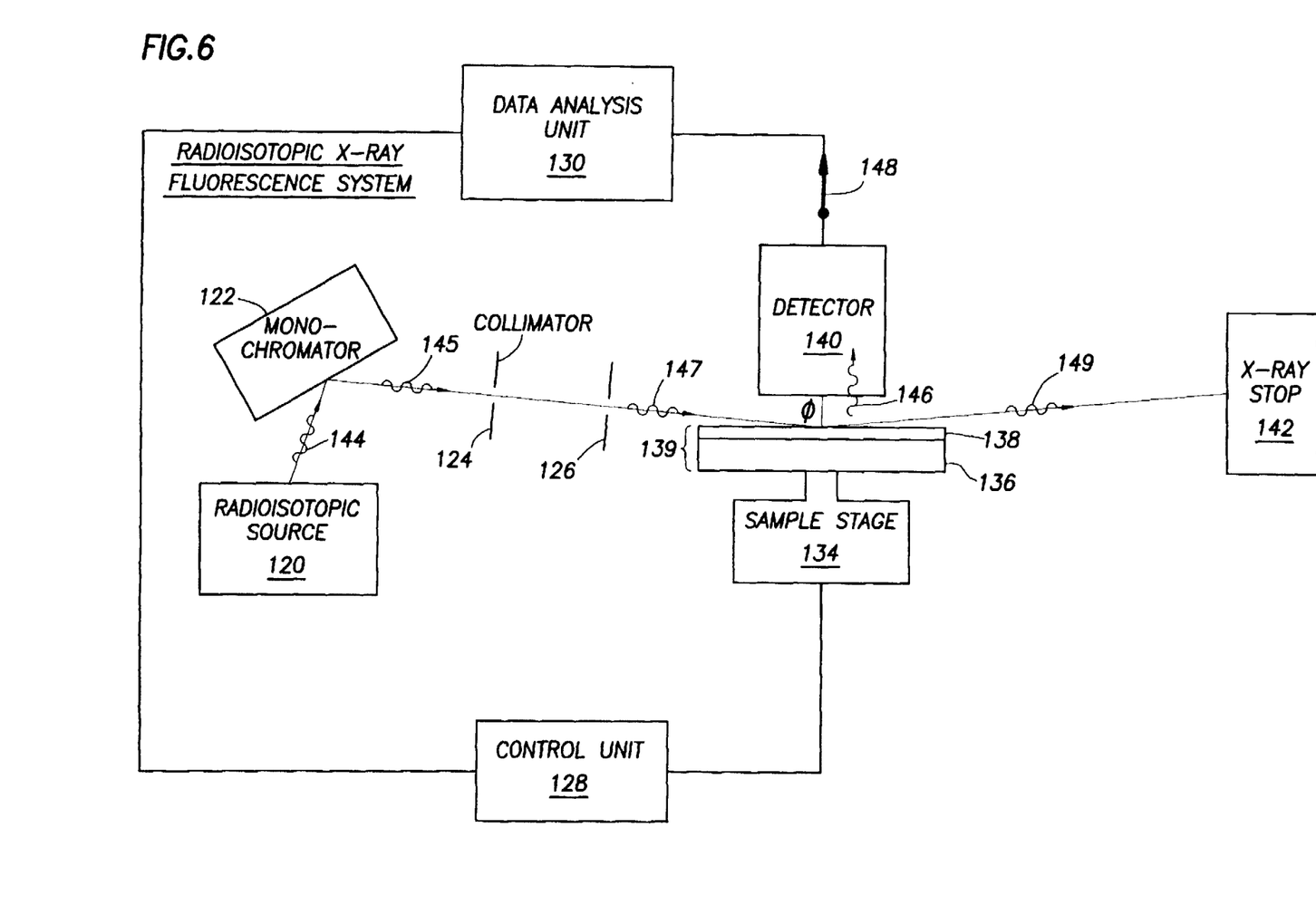
FIG. 6 is the apparatus of the present invention comprising an X-ray fluorescence spectrometer utilizing a radioisotopic source.

FIG. 6 depicts a preferred embodiment of the current invention, a radioisotopic X-ray fluorescence system. The system consists of a radioisotopic X-ray source 120, configured to produce a beam of primary X-ray photons 144. Radioisotopic source 120 could include elements such as $^{55}$Fe, $^{109}$Cd, or $^{241}$Am.

Because of their important role in producing an inexpensive, compact, portable, method of thin film metrology, radioisotopic sources should be considered with some degree of detail. Radioactive decay processes may be put into the following categories: γ decay, α decay, β decay, and electron capture (a form of β decay).

γ decay comes about from the de-excitation of a nucleus in an excited state. Similar to electrons, the energy states of a nucleus are quantized—that is, a nucleus has a discrete energy within an allowed energy spectrum. As was the case with electrons, a nucleus may make transitions between quantized states. When a nucleus makes a transition from a higher to a lower energy state, energy conservation principles dictate that the excess energy associated with the transition (represented by the difference in energy values of the initial and final quantized states) must be released. The energy associated with such a nucleus state transition is a γ photon.

α decay occurs mostly in certain radioactive heavy nuclei with proton numbers greater than 82. In a decay, an unstable parent nuclei may spontaneously decay into a daughter nucleus and a stable helium nucleus (an α particle). Most α emitters exhibit a discrete range of α particle energies. This discrete energy range can be understood by considering that upon an α decay, the daughter nuclei may be in any one of a number of quantized states. If the parent nuclei decays into the excited state of a daughter nuclei, the a particle emitted will have a lower energy than if the parent nuclei were to decay into the ground state of the daughter nuclei. Approximately 160 α emitters have been identified and their emitted α particles have discrete energies ranging anywhere from about 4 to 10 MeV.

β decay is a decay process in which the charge of a nucleus is changed while the number of nucleons remains constant. There are four basic reactions associated with β decay, and each will be discussed briefly, in turn, to explain the β decay process. The following are the four basic reactions:

| | |
|---|---|
| 1) n → p + e + $\bar{\upsilon}$ | β⁻ decay |
| 2) p → n + e⁺ + ν | β⁺ decay |
| 3) e + p → n + ν | Electron capture |
| 4) $\upsilon$ + p → n + e⁺ | Neutrino absorption |

β⁻ decay, a neutron within a parent nucleus is converted into a proton and neutron, along with the release of a neutrino. Such a decay is accompanied by a weak continuous electromagnetic spectrum of Bremsstrahlung radiation produced when the released electron is slowed while passing through the source material. However, such braking radiation only provides a low background spectrum, varying slowly with energy, in a limited region of the radiating sample. Thus, it presents no serious problems for spectroscopic applications which may make use of β⁻ emitters.

β⁺ decay involves the conversion of a proton within a nucleus to a neutron, positron, and neutrino. This decay process also is accompanied by a weak electromagnetic background of Bremsstrahlung radiation.

Electron capture is of particular interest because it is accompanied by the production of characteristic X-rays. In this process, an electron is literally captured by a nucleus of an atom and when combined with a proton is converted into a neutron and a neutrino. When a K-shell electron is absorbed into the nucleus, a vacancy is created in the inner shell of the parent element. As this vacancy is filled, an X-ray characteristic of the daughter element is released.

In the final type of β⁻ decay process, a neutrino and proton decay into a neutron, emitting a positron. In this decay scheme, a weak background of braking radiation is present due to the slowing down of the positron as it travels through the source material.

Following an α or β decay process, the daughter nucleus may be in an excited state. Upon making a transition to a lower, or ground state, the nucleus may release, as discussed above, γ radiation. However, similar to the production of Auger electrons within an atom, the γ radiation produced following a decay may interact with an electron in the atom and transfer its energy to that electron, ejecting it from the atom. Such a process is termed internal conversion. Following internal conversion, the ionized atom will decay with the production of X-ray radiation characteristic of the daughter nucleus.

Besides internal conversion and electron capture, X-rays may also be produced using radioisotopes via a process termed external Bremsstrahlung. In this process, a radioactive nucleotide emits β particles which are incident upon a target material. As the β particles are slowed within the target material, continuous (not characteristic) braking X-ray radiation is emitted. This X-ray radiation may then be used as a primary source of X-rays in spectroscopy equipment.

Characteristic X-ray radiation may also be produced using radioisotopic sources by allowing the radioisotopic source to excite characteristic X-ray radiation from a target material. A β or γ emitter held in close proximity to a target material will emit β or γ particles which strike the target material. The impacting particles cause electron transitions within the target atoms. Vacancies resulting from such transitions are subsequently filled and characteristic X-ray radiation is released.

Although offering an intensity orders of magnitude smaller than that of high powered sources used today in XRF equipment, radioisotopic sources which emit radiation by processes such as the ones described above, are well suited for characterizing minor components embedded within thin film. Because the components being measured in the current invention do not have trace concentrations, sensitivity and background problems do not present an insurmountable hurdle for this method. Thus, a powerful, complicated X-ray tube, rotating anode source, or synchrotron source is not needed. In fact, such a high power source would not allow the current method to be used as a portable, inexpensive apparatus.

Radioisotopes are small, light, stable, and inexpensive. They have no moving parts. The only maintenance required is exchanging sources once the decay processes, over time, diminish. Radioisotopic sources may achieve excitation energies sufficient for the present application—exciting minor components within a thin film. Excitation energies of 100–150 keV may be obtained with radioisotopic sources. Such energies are more than sufficient for exciting K lines of the heaviest elements. Because of the monochromatic nature of much of radioisotopic sources, a source may be chosen which is specifically targeted for exciting a particular line within a thin film, while not exciting other elements which need not be studied or measured.

The primary beam of X-ray photons 144 produced by source 120 is incident upon monochromator 122. Monochromator 122 consists of multiple layers of materials and is configured to receive primary X-ray beam 144 and to strongly reflect X-ray photons with a certain wavelength (or corresponding energy level), producing a monochromatic primary X-ray beam 145.

Multilayer monochromator 122 may be a crystal structure made up of many alternating layers of heavy and light elements (e.g., tungsten and carbon). Such multilayer crystals are also called multilayer mirrors. Each layer of a typical multilayer crystal is only a few atoms thick, and has an index of refraction which is different from the other layer. When an incident X-ray beam strikes a planar surface of a multilayer crystal at an angle, a small fraction of the incident X-ray beam is reflected at a planar upper surface of the multilayer crystal and at each interface between alternating layers. Reflected X-ray photons which are in phase and reinforce each other form a strongly-reflected monochromatic X-ray beam. Contributions from reflected X-ray photons which are not in phase interfere with one another, largely canceling each other out. The angle of incidence formed between incident primary X-ray beam 144 and the planar upper surface of multilayer monochromator 122 is adjusted to produce a monochromatic primary X-ray beam 145 made up of primary X-ray photons with a given wavelength (or corresponding energy level.

Monochromatic primary X-ray beam 145 is then incident upon a set of collimators 124 and 126. These collimators produce a quasi-parallel X-ray beam 147. Collimators 124 and 126 are preferably Soller-type collimators having a bundle of straight, hollow metal conduits. Fine collimation is obtained using spacings of about 1.0 micron between opposite walls of the individual square conduits making up the collimator. Suitable Soller-type collimators are commercially available from the Philips Co., Mahwah, N.J.

After passing through collimators 124 and 126, primary X-ray beam 147 is incident upon an exposed region of sample 139. Sample 139 consists of a thin film 138 positioned upon a semiconductor topography or substrate 136. Thin film 138 might typically be 250 Angstroms thick and, according to one embodiment, can be composed of titanium doped with minor concentrations of silicon, for example. Semiconductor substrate 136 is made of silicon. The angle of incidence of beam 147 upon sample 139 is denoted by φ and ranges from 89.99 to 85.00 degrees. The use of such a large angle of incidence serves many purposes. One advantage of using such an angle is that the depth of penetration within the sample is limited. The larger the angle of incidence, the less beam 147 penetrates into sample 139. Thus, adjusting angle φ can ensure that elements embedded within layers underneath thin film 138 are not excited. Another advantage associated with large φ is that background radiation is reduced drastically, allowing for better overall quantitative analysis of the elements embedded within thin film 138.

Beam 147 impacting sample 139 at an angle φ excites atoms within thin film 138 and causes electron transitions therein. Angle φ, radioisotopic source 120, collimators 124 and 126 may all, individually or in combination, be adjusted so that only atoms within thin film 138 undergo transitions. As stressed before, accurate characterization of thin film 138 requires a method and apparatus which produces secondary X-ray emission from a thin film while not producing such emissions from underlying layers. As electron vacancies in thin film 138 are filled, characteristic secondary X-ray photons 146 are emitted only from thin film 146.

Secondary X-ray photons 138 are detected by detector 140 which is positioned directly above sample 139 and is configured to produce output signals 148 in response to receiving radiation 146. Detector 140 is positioned above sample 139 so that background radiation may be reduced and so that sensitivity and quantitative results may thereby be improved. Conventional XRF detector arrangements (where the detector is placed "downstream" from the sample) are such that detectors receive a substantial portion of scattered primary radiation. This increases background radiation and makes reliable quantitative results more difficult. The current invention, utilizing high angles of incidence and a detector placed directly above the sample, eliminates most of the problems associated with excessive background counts. Detector 138 may be a proportional X-ray detector, a scintillation detector, or a lithium-drifted silicon detector.

Proportional counters consist of a wire mounted along the central axis of a cylindrical container and filled with an inert gas to a pressure of approximately one atmosphere. The centrally-mounted wire is held at a positive potential relative to the inert gas and produces a uniform electric field within the cylindrical container. Proportional counters depend upon the ionization caused when an energetic photon interacts with a gas. Energetic secondary radiation such as radiation 146, upon entering a proportional detector, ionizes an atom of gas within the cylindrical container. The free electron created by this ionization is then accelerated toward the positively biased central wire. While accelerating towards the central wire, the free electron collides with other gas particles, ejecting electrons along the way. As more electrons are ejected, more electrons rush towards the positively biased wire, causing even more collisions and more electron ejection. Such a process whereby one ejected electron creates a multiplicity of free electrons is termed an avalanche effect. A typical avalanche effect results in the production of $10^4$ electrons from a single electron ejection from a primary beam such as 146. As vacancies are filled resulting from the ejection of electrons, characteristic X-rays or Auger electrons are ejected into the cylindrical container. Such X-rays and Auger electrons are reabsorbed into the gas or accelerated towards the central wire, respectively.

The free electrons created by the avalanche effect reach the central wire in the proportional counter and create a voltage pulse. All such voltage pulses are then counted using a counter circuit. The height of the voltage pulses is proportional to the energy of the secondary beam of radiation incident upon the detector—in this exemplary case, secondary X-ray photons 146. The height of the pulse is proportional to the energy of the incident radiation because the number of ion pairs formed by X-ray ionization is proportional to the energy of the radiation, and the number of ion pairs is proportional to the height of the pulse.

Scintillation detectors consist usually of a sodium iodide crystal doped with thallium. X-rays absorbed in a scintillation detector transfer their energy to photoelectrons whose energy are, in turn, transformed by the crystal into light pulses of about 3 eV. The more energetic the incident X-rays, the more light pulses are produced. The light pulses are then incident upon a photomultiplier. The photomultiplier converts the light pulses to voltages signals which are collected and amplified. The output of a scintillation detector is therefore proportional to the energy of incident radiation, such as radiation 146 in FIG. 6, and consists of a pulse-height distribution for each incident x-ray wavelength.

Lithium-drifted silicon detectors (Si(Li) detectors) have become very common in the field of X-ray spectroscopy. Si(Li) detectors consist of a single-crystalline disk of semiconductor-grade silicon having an intrinsic region formed by drifting lithium into p-type silicon sandwiched between p and n-type regions. A Schottky barrier contact on the front of the disk produces a p-i-n diode. A reverse bias of 800–1000 V is applied to the detector.

As X-ray photons enter a Si(Li) detector, they transfer their energy to photoelectrons which produce a number of electron-hole pairs. The number of electron-hole pairs produced is proportional to the energy of the incident X-ray photons. The charge represented by the electron-hole pairs is swept out of the detector by the bias voltage of the detector and induces a signal at the gate of a field effect transistor (FET). This signal is then typically fed to a charge-sensitive preamplifier which produces a pulse proportional to the incident X-ray photon energy. The detector, FET, and preamplifier are all cooled using liquid nitrogen. Such cooling reduces electronic noise and ensures optimal resolution when the detector is in use.

Sample 139 is held by sample stage 134 which is configured to adjust angle of incidence φ by tilting or moving sample 139 in the x, y, or z directions. Sample 139 may be held in place upon stage 134 by any appropriate means, such as by flowing helium gas along the backside of 139, creating a force holding sample 139 firmly against stage 134.

Stage 134 is coupled to control unit 128. Control unit 128 is configured to automatically adjust stage 134 in any appropriate manner in response to output signals 148 from detector 140.

Data analysis unit 130 is coupled to detector 140 and to control unit 128. Data analysis unit 130 is configured to analyze the data represented by output signals 148. More specifically, data analysis unit 130 counts the number of secondary X-ray photons 146 received in detector 140 and determines their respective energies by analyzing the signals 148 generated by detector 140. Data analysis unit 130 also comprises the means to display or manipulate any of the information extractable from output signals 148.

X-ray stop 142 is any device or material whose purpose is to stop X-ray beam 149. X-ray stop 142 may consist of a scintillation detector, a proportional counter, a solid, a shield, or any other appropriate apparatus.

Figure 7:
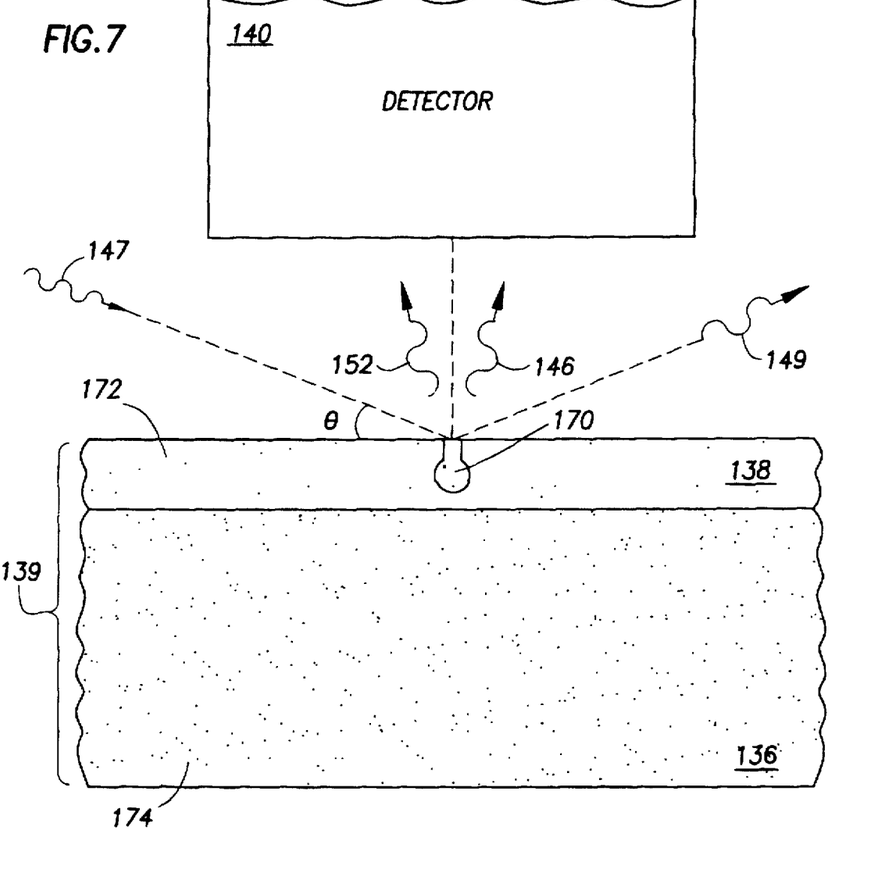
FIG. 7 is an expanded, more detailed view of the sample region of the apparatus which shows the emission of secondary X-ray photons into an X-ray detector.

FIG. 7 is an enlarged view of the sample region of FIG. 6. Primary beam 147 impinges upon sample 139 producing secondary X-ray photons 146 and 152 which are received by detector 140. Radiation 149 is scattered from sample 139 towards an X-ray stop (not shown in this figure).

Shown in FIG. 7 is the angle θ, the complement of angle φ of FIG. 6. Angle θ may range anywhere from 0.01 to 5.00 degrees. Upon impacting thin film 138 at angle θ, atoms 172 within region 170 are excited so that electron transitions occur in atoms 172 residing within thin film 138. Vacancies are filled in atoms 172 within region 170 by electron transitions from energy states higher than the state in which the vacancy has occurred. Transitions from higher to lower energy states cause characteristic secondary photons 146 and 152 to be emitted from thin film 138.

Also shown in FIG. 7 is semiconductor substrate 136. 174 denotes atoms embedded within substrate 136. The parameters of incident radiation 147 are such that atoms 174 emit no detectable secondary X-ray photons. In other words, region 170 does not extend into substrate 174.

Figure 8:
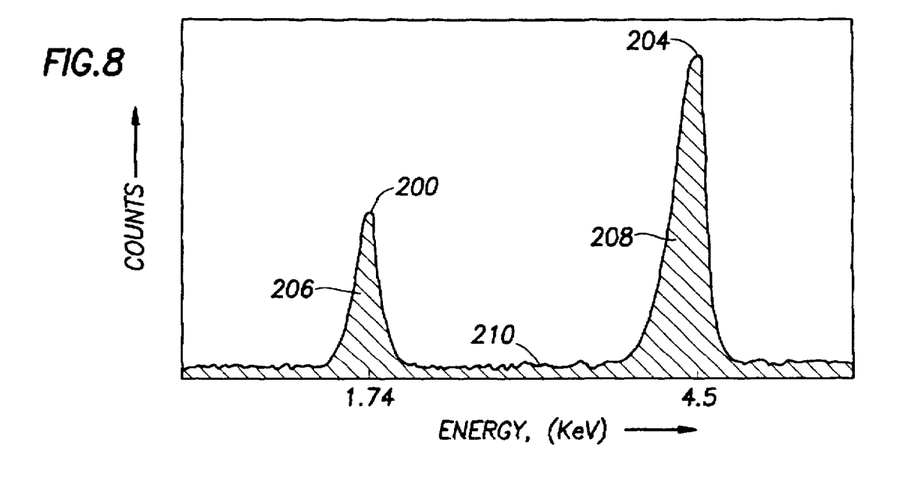
FIG. 8 illustrates the data analysis scheme of the present invention.

FIG. 8 depicts hypothetical data resulting from the measurement of silicon embedded within a thin film (approximately 250 angstroms) of titanium. Shown in FIG. 8 are two peaks, 200 and 204 and a background intensity 210. In the silicon-embodied exemplary silicon example, peak 200 is shown centered about 1.74 keV. Peak 200 represents the silicon embedded within the thin film being studied. Peak 204, centered about 4.5 keV represents titanium within the film.

To determine the quantity of silicon embedded within the thin film, one may determine the ratio of the area 206 under the silicon peak to the area 208 under the titanium peak. Such a calculation would indicate that the thin film contained a certain percentage of silicon relative to titanium.

One might also correlate area 206 with a corresponding area produced by regression data taken from a calibration sample (a standard) which was analyzed under similar conditions. Thus, one might determine that an area 206, obtained under certain conditions (conditions such as detection time, primary X-ray energy, etc.) corresponds to a certain concentration of silicon in units of atoms per cm$^2$.

Quantitative analysis might also consist of correlating area 206, using a look-up table or regression data, with a certain relative concentration of silicon. Thus, one might determine that area 206, representing the amount of silicon embedded within a titanium thin film, corresponded to a certain percent composition of silicon (relative to titanium).

What is claimed is:

1. An apparatus for determining the identity and quantity of a targeted atomic species embedded within a film, comprising:
   a radioisotopic X-ray source configured to produce a beam of x-ray photons;
   a stage adapted for securing a semiconductor topography upon which a film extends thereacross, said film having a substantially planar upper surface;
   a control unit coupled to said stage for fixing an angle of incidence of said beam of x-ray photons upon said film within the range of 0.01 and 5.00 degrees relative to said planar surface;
   a detector configured directly above the point in which said beam of x-ray photons are incident upon said film for detecting secondary x-ray photons emitted from said targeted atomic species as well as other atomic species embedded within said film;
   a data analysis unit coupled to said detector for discerning said targeted atomic species from said other atomic species within said thin film; and
   an electrical coupling between said data analysis unit and said control unit for changing said angle of incidence to optimize the amount of secondary x-ray photons emitted from said targeted atomic species only within said film.

2. The apparatus as recited in claim 1, wherein said targeted atomic species comprise silicon.

3. The apparatus as recited in claim 1, wherein said other atomic species comprise titanium.

4. The apparatus as recited in claim 1, wherein said radioisotopic source is selected from the group consisting of $^{55}$Fe, $^{109}$Cd, and $^{241}$Am.

5. The apparatus as recited in claim 1, wherein said detector produces electrical signals proportional to the energy of secondary X-ray photons received by said detector.

6. The apparatus as recited in claim 1, wherein said detector is a lithium-drifted silicon detector.

7. The apparatus as recited in claim 1, wherein said detector is a scintillation X-ray detector.

8. The apparatus as recited in claim 1, wherein said detector is a proportional X-ray detector.

9. The apparatus as recited in claim 1, wherein said control unit changes said angle of incidence to ensure said beam of x-ray photons does not penetrate below said film and into said semiconductor topography.

10. An apparatus for determining the identity and quantity of elements embedded within a film positioned upon an underlying semiconductor substrate, comprising:
    a radioisotopic source producing a beam of primary x-ray photons;
    a monochromator aligned to receive said beam and configured to produce a monochromatic primary beam of x-ray photons;
    at least one collimator aligned to receive said primary beam and configured to produce a quasi-parallel primary x-ray beam incident upon an exposed region of a sample, said exposed region comprising said thin film positioned upon said underlying semiconductor substrate;
    a stage holding said sample and configured to adjust the angle of incidence of said primary x-ray beam upon the surface of said sample so that atoms embedded within said film emit secondary X-ray photons while atoms within said underlying substrate do not substantially emit secondary X-ray photons; and
    an X-ray detector positioned adjacent to said exposed region to receive secondary x-ray photons emitted by atoms embedded within said film, said x-ray detector configured to produce electrical output signals in response to receiving said secondary x-ray photons.

11. The apparatus as recited in claim 10, wherein said radioisotopic source is selected from the group consisting of $^{55}$Fe, $^{109}$Cd, and $^{241}$Am.

12. The apparatus as recited in claim 10, wherein said stage holding the sample may be tilted and moved in the x, y, and z directions to achieve said angle of incidence at which secondary X-ray photons are emitted by atoms embedded within said thin film while secondary X-ray photons are not substantially emitted by atoms within said underlying substrate.

13. The apparatus as recited in claim 10, wherein said detector comprises a lithium-drifted silicon detector.

14. The apparatus as recited in claim 10, wherein said detector is a scintillation X-ray detector.

15. The apparatus as recited in claim 10, wherein said detector is a proportional X-ray detector.

16. The apparatus as recited in claim 10, further comprising a control unit coupled to said stage holding the sample and said X-ray detector, wherein said control unit comprises means for adjusting said angle of incidence automatically in response to said output signals produced by said detector.

17. A method for determining the identity and quantity of a targeted atomic species embedded within a film positioned upon an underlying semiconductor substrate, comprising the steps of:
    exposing the surface of said film to a beam of primary x-ray photons emitted from a radioisotopic source, wherein the angle of incidence of said beam upon said surface is suitably chosen so that said targeted atomic species emit secondary x-ray photons while other atomic species within said underlying semiconductor substrate do not substantially emit secondary X-ray photons;
    positioning an x-ray detector a spaced distance directly above the point in which said beam in incident upon the surface of said film, said detector configured to produce output signals in response to receiving secondary x-ray photons emitted by said targeted atomic species within said film; and
    counting the number of secondary X-ray photons received by said detector having a specified energy, said energy determining the identity of a said targeted atomic species exclusively within said film while said number determining the quantity of said targeted atomic species exclusively within said film.

18. The method as recited in claim 17, wherein said targeted atomic species comprises silicon.

19. The method as recited in claim 17, wherein said quantity of elements embedded within said thin film is greater than $10^{15}$ atoms/cm$^2$.

20. The method as recited in claim 17, wherein said radioisotopic source is selected from the group consisting of $^{55}$Fe, $^{109}$Cd, and $^{241}$Am.

21. The method as recited in claim 17, wherein said angle of incidence, measured with respect to a substantially planar upper surface of said film ranges from 0.01 degree to 5.00 degrees.

22. The method as recited in claim 17, wherein said output signals are proportional to the energy of secondary x-ray photons received by said detector.

23. The method as recited in claim 17, wherein said counting is performed for a predetermined duration of time.

24. The method as recited in claim 17, wherein said counting comprises plotting the number of secondary x-ray photons received by said detector versus the energy of said secondary x-ray photons received by said detector.

25. The method as recited in claim 24, wherein a plot of said number of secondary x-ray photons received by said detector versus the energy of said secondary x-ray photons received by said detector comprises at least a first and second peak, wherein either said first or second peak corresponds to said targeted atomic species.

26. The method as recited in claim 25, wherein said first peak corresponds to silicon atoms and said second peak corresponds to titanium atoms.

27. The method as recited in claim 26, wherein said quantity of said targeted atomic species is determined as a relative percentage by calculating the ratio of the area under said first peak in said plot to the area under said second peak in said plot.

28. The method as recited in claim 27, wherein said quantity of said targeted atomic species is determined by correlating said first peak with linear regressions derived from the analysis of appropriate standards.

29. The method as recited in claim 27, wherein said quantity of said targeted atomic species is determined with linear regression data which correlates the relative quantity of said targeted atomic species represented by said first peak with the area under said first peak in said plot.

* * * * *